US007741066B2

(12) United States Patent
Liu (10) Patent No.: US 7,741,066 B2
(45) Date of Patent: Jun. 22, 2010

(54) PHOSPHORYLATED P68 RNA HELICASE AS A MARKER FOR CANCER AND CANCER METASTASIS

(76) Inventor: Zhi-Ren Liu, 2466 Nancy La., NE., Atlanta, GA (US) 30345-1923

( * ) Notice: Subject to any disclaimer, the term of this patent is extended or adjusted under 35 U.S.C. 154(b) by 0 days.

(21) Appl. No.: 11/361,258

(22) Filed: Feb. 24, 2006

(65) Prior Publication Data

US 2008/0014597 A1   Jan. 17, 2008

Related U.S. Application Data

(60) Provisional application No. 60/655,786, filed on Feb. 24, 2005.

(51) Int. Cl.
G01N 33/574   (2006.01)
(52) U.S. Cl. .......................... 435/7.23; 435/7.1
(58) Field of Classification Search .................. None
See application file for complete search history.

(56) References Cited

U.S. PATENT DOCUMENTS

| 6,613,534 | B2 | 9/2003 | Setaluri et al. | |
|---|---|---|---|---|
| 2007/0072235 | A1* | 3/2007 | Moritz et al. | 435/7.1 |

FOREIGN PATENT DOCUMENTS

WO   2007068478 A   6/2007

OTHER PUBLICATIONS

Tockman et al, Cancer Res., 1992, 52:2711s-2718s.*
Slamon et al., Science vol. 235, Jan. 1987, pp. 177-182.*
Compton et al, Mod Pathol, 2003, 16:376-388.*
Yang et al, Protein Expression Purification, 2004, 35:327-333.*
Online IHOP, alternate names for p68 RNA helicase, Sep. 24, 2008.*
Halfteck et al, J Immunol, 2009, 182:2221-2230.*
Britton, et al.; Bidirectional cross talk between ER_and EGFR signalling pathways regulates tamoxifen-resistant growth; Breast Cancer Research & Treatment; Oct. 27, 2005; pp. 1-16; Cardiff University, Cardiff, UK.
Yang, et al.; Phosphorylations of DEAD Box p68 RNA Helicase are Associated with Cancer Development and Cell Proliferation; Mol Cancer Research; Jun. 2005; pp. 1-10.
Kahlina, et al.; p68 DEAD Box RNA Helicase Expression in Keratinocytes; Oct. 22, 2004; pp. 44872-44882; vol. 279, No. 43, JBC Papers in Press.
Yang, et al; Phosphorylation of p68 Helicase Regulates RNA Binding by the C-terminal domain of the Protein; Biochemical and Biophysical Research Communications 314; 2004; pp. 622-630; Elsevier, Inc.
Causevic, et al.; Overexpression and Poly-Ubiquitylation of the DEAD-box RNA Helicase p68 in Colorectal Tumours; Oncogene; 2001; pp. 7734-7743; Nature Publishing Group.
Partridge, et al; Molecular Markers for Diagnosis and Prognosis; Cancer and Metastasis Reviews; 2005, pp. 71-85, Springer Science and Business Media, Inc., The Netherlands.
Weigelt, et al; Breast Cancer Metastasis: Markers and Models; Nature Reviews, Aug. 2005, pp. 591-602; vol. 5, Nature Publishing Group.
Stevenson, et al; Expression of the 'Dead Box' RNA Helicase p68 is Developmentally and Growth Regulated and Correlates with Organ Differentiation/Maturation in the Fetus; Journal of Pathology,1998, pp. 351-359, vol. 184, John Wiley & Sons, Ltd.
International Search Report and Written Opinion.
The DEAD box protein p68: a novel transcriptional coactivator of the p53 tumour suppressor, Gates, Gaynor J., et al., The EMBO Journal (2005), 24-543-553.
Liu, Zhi-Ren, p68 RNA helicase is an essential human splicing factor that acts at the U1 snRNA 5' splice site duplex, Molecular and Cellular Biology, Aug. 2002, vol. 22, No. 15, p. 5443-5450, American Society for Microbiology, Washington DC.
Lin, Chunru, ATPase/Helicase Activities of p68 RNA Helicase Are Required for Pre-mRNA Splicing but Not for Assembly of the Spliceosome; Molecular and Cellular Biology, Sep. 2005; p. 7484-7493; vol. 25, No. 17.
European Search Report, dated Nov. 12, 2008.
Causevic, M., et al., "Over expression and Poly-Ubiquitylation of the Dead-Box RNA Helicase p68 in Colorectal Tumours," Oncogene, Nature Publishing Group, GB Basingstoke, Hants, vol. 2, Jan. 1, 2001 pp. 7734-7743.
Yang, L., et al., "Phosphorylations of Dead Box p RNA Helicase are Associated with Cancer Development and Cell Proliferation", Molecular Cancer Research, American Association for Cancer Research, vol. 3, No. 6, Jun. 1, 2005, pp. 355-363.
Abdelhaleem M. "Do Human RNA Helicases Have a Role in Cancer?" BBA-Reviews on Cancer, Elsevier science, BV, Amsterdam, NL, vol. 1704, No. 1, Jul. 6, 2004, pp. 37-46.
Yang, L., et al. "Bacterially Expressed Recombinant p68 RNA helicase is Phosphorylated on Serine, Threonine, and Tyrosine Resides", Protein Expression and Purification, Academic Press, San Diego, CA vol. 35, No. 2, Jun. 1, 2004 pp. 327-333.

* cited by examiner

*Primary Examiner*—Misook Yu
*Assistant Examiner*—Mark Halvorson
(74) *Attorney, Agent, or Firm*—Nigamnarayan Acharya; Barnes & Thornburg LLP (57) ABSTRACT

A method for determining the presence of cancer cells in a tissue sample or cell sample by detecting the presence of phosphorylated p68 RNA helicase in the sample. Further, a method for determining the presence of metastatic cancer cells in a tissue sample or cell sample by detecting the level of phosphorylated P68 RNA helicase in the sample such that a greater level of the phosphorylated protein in the sample as compared to non-metastatic cells is an indication of the metastatic cancer cells in the sample.

9 Claims, 6 Drawing Sheets

PHOSPHORYLATED P68 RNA HELICASE AS A MARKER FOR CANCER AND CANCER METASTASIS

STATEMENT OF RELATED APPLICATIONS

This application is a non-provisional patent application claiming priority on U.S. Provisional Patent Application No. 60/655,786 entitled "Phosphorylated P68 RNA Helicase as A Marker for Cancer and Cancer Metastasis" having a filing date of 24 Feb. 2005, which is incorporated by reference.

STATEMENT REGARDING FEDERALLY SPONSORED RESEARCH OR DEVELOPMENT

This invention was made with government support under 5 R01 GM063874 awarded by the National Institute of Health. The U.S. government has certain rights in the invention.

BACKGROUND OF THE INVENTION

1. Technical Field

This invention relates generally to the field of cancer diagnostics and to markers for use in the diagnosis, prognosis, and treatment of cancer, including for determining cancer metastasis.

2. Prior Art

Cancer is the second leading cause of human death next to coronary disease. In the United States, cancer causes the death of over a half-million people each year and about two million new cases of cancer are diagnosed each year. Cancer has become the leading cause of death in the United States and abroad. However, a cancer patient is more likely to be successfully treated with an early diagnosis. Further, the chances of successfully treating a patient improve substantially when the patient has been treated prior to cancer metastasis.

The identification of tumor markers for diagnostic purposes has been an objective of cancer research over the past several decades. Markers produced in cells or tissues have been sought after as such markers are useful in the diagnosis and treatment of cancer and in the identification of cancer metastasis. The measurement of tumor marker levels may be useful in the detection of some types of cancer. Further, quantifying the flux of marker levels may be useful in determining or evaluating the effectiveness or course of treatment. As such, the search for cancer markers is paramount.

In search of a tumor marker, the inventor has investigated p68 RNA helicase. Nuclear p68 RNA helicases (e.g. sequence ID. Nos. 1 and 2) are a prototypical member of the DEAD-box family of helicases, distinguished by a core characteristic sequence of Asp-Glu-Ala-Asp (DEAD). P86 RNA helicase was found to be phosphorylated at tyrosine residue(s) in HeLa cells. Yang et al., Phosphorylation of p68 RNA Helicase regulates RNA Binding by the C-terminal Domain of the Protein, *Biochem. Biophys Res Commun*, 314:622-30 (2004). In a previous study, it was shown that p68 RNA helicase was over-expressed in colorectal cancer tissues and cancer cell lines. Based upon these findings, the inventor pursued p68 RNA helicase as a potential cancer marker.

Accordingly, there is always a need for improved diagnostic tools for cancer and cancer metastasis. Further, there is always a need for methods and tools for determining and evaluating the effectiveness or course of treatment of cancer. Further, such new methods and tools can be useful for identifying metastasis cancer. It is to these needs, among others, that the present invention is directed.

BRIEF SUMMARY OF THE INVENTION

Briefly, this invention involves the use of phosphorylated p68 RNA helicase as a cancer maker, a marker for cancer metastasis, and a potential therapeutic target for cancer cells. While p68 RNA helicase is expressed in normal cells as well as cancerous cells, it was found that the p68 RNA helicase is phosphorylated in cancer cells including metastatic cancer. In fact, the phosphorylation status of p68 RNA helicase in a cell appears to correlate with an identification of that cell as cancerous and with an identification of that cell as metastatic cancer cell. More particularly, phosphorylated p68 RNA helicase represents a cancer marker that can be used to discriminate between cancer cells and normal cells. Further, the phosphorylated p68 RNA helicase can provide potential therapeutic target in cancer treatments.

One method of this invention for determining the presence of cancer cells in a tissue sample comprises the steps of providing a tissue sample from a patient and detecting phosphorylated p68 RNA helicase in the sample. In this method, the detection of the phosphorylated p68 RNA helicase in the tissue sample is an indication of cancer cells in the tissue sample. The tissue sample can be from, for example, a bladder, brain, breast, colon, esophagus, kidney, lung, lymph node, ovary, skin, stomach, testis, or uterus.

The phosphorylation status of p68 RNA helicase in six different cancer cell lines was compared to the corresponding cell lines derived from the normal tissues. The comparison demonstrated that p68 RNA helicase was phosphorylated at tyrosine residue(s) in all tested cancer cells but not in the corresponding normal cells. More particularly, the p68 RNA helicase was phosphorylated at tyrosine residue(s) in six different cancer cell lines, but not in cell lines derived from corresponding normal tissues. As such, the phosphorylation status of p68 RNA helicase can be a marker for cancer or cancerous cells.

The presence of phosphorylated p68 RNA helicase in many types of cancer demonstrates that this p68 RNA helicase may have an endogenous function in cancer cells. Its identification in a diverse range of cancers of different histogenetic types and its absence from normal tissues suggests that phosphorylated p68 RNA helicase is one of the common changes of a gene product in malignancy. P68 RNA helicase is linked to cell growth signals, especially the mechanism by which p68 RNA helicase dysfunctions in the cancer development process. As such, p68 RNA helicase has a role in tumor development and progression and may provide for an effective therapeutic target.

DETAILED DESCRIPTION OF THE PREFERRED EMBODIMENTS

Illustrative embodiments of the present invention relate to the use of phosphorylated p68 RNA helicase as a cancer maker. While p68 RNA helicase is expressed in both normal cells and cancer cells, p68 RNA helicase is phosphorylated in cancer cells, and in metastatic cancer cells. The phosphorylation of p68 RNA helicase in a cell appears to correlate with an identification of that cell as cancerous or as metastatic. As such, the phosphorylation of p68 RNA helicase in a patient may be indicative of cancer and the level or site of phosphorylation may be indicative of cancer metastasis.

More particularly in this invention, p68 RNA helicase was found to be phosphorylated in different types of cancers that developed in a broad range of different anatomical sites. For example, p68 RNA helicase is phosphorylated in all cancer cells from lungs, colons, livers, breasts, kidneys and lymphocytes. The nuclear p68 RNA helicase is tyrosyl phosphorylated in six different cancer lines but not in the cell lines derived from each corresponding normal tissue. Thus, the close correlation between p68 RNA helicase tyrosyl phosphorylation(s) and cancer and cancer metastasis can be a useful diagnostic marker for cancer.

In one embodiment, phosphorylated p68 RNA helicase represents a cancer marker that can be used to discriminate between cancer cells or metastatic cells and normal cells. In one preferred embodiment, immunoreactivity of phosphorylated p68 RNA helicase correlated well with cancer cells. In contrast, noncancerous or normal cells showed no immunoreactivity for phosphorylated p68 RNA helicase.

Further, phosphorylated p68 RNA helicase represents a cancer marker that can be used to reflect the stages of cancer. It was found that the level of p68 RNA helicase phosphorylation corresponded to different stages of cancer progression. Specifically, higher levels of phosphorylated p68 RNA helicase were found in metastatic cancer, whereas lower levels were found to correlate with non-metastatic adenocarcinoma (adenoCA) cells. In many cases, the level of p68 RNA helicase phosphorylation in metastatic cells was substantially (e.g. over two-fold) higher than in non-metastatic cancerous tissue. The close correlation between the level of p68 RNA helicase phosphorylation and metastatic cancer is useful in evaluating the staging of cancer in patients.

One preferred method of using phosphorylated P68 RNA helicase to screen cancer cells includes the steps of:

(1) obtaining a tissue or cell sample to be tested for the presence of cancer cells;

(2) preparing the sample for screening;

(3) testing the sample with a recognition agent, such as an antibody, that reacts with human phosphorylated p68 RNA helicase; and (4) detecting the presence of the phosphorylated p68 RNA helicase by detecting the binding of the recognition agent to phoshorylated p68 RNA helicase, if present, in the prepared sample. The tissue or cell samples can be extracted from organs such as the bladder, brain, breast, colon, esophagus, kidney, lung, lymph node, ovary, skin, stomach, testis, and uterus. In one embodiment, the tissue sample is extracted form a human or a human having cancer.

The recognition agent can be an antibody, as this type of recognition agent is typically more useful in screening laboratories. In such an embodiment, antigen binding domain fragments of antibodies can be Fab fragments. Furthermore, RNA aptomers may be used with this invention. Antibodies suitable with this invention include polyclonal or monoclonal antibodies. Optionally, the antibody can be produced by a method so that the antibodies recognize a pre-selected epitope of the phosphorylated p68 RNA helicase.

Antibodies may be commercially available, or may be prepared by methods standard in the art. In one embodiment, polyclonal antibody to phosphorylated p68 RNA helicase is prepared by injection of phosphorylated p68 RNA helicase supplemented with an adjuvant using methods known in the art. For example, polyclonal antibodies are a heterogeneous population of antibody molecules derived from the sera of animals immunized with the antigen of interest. Adjuvants such as Freund's (complete and incomplete), peptides, oil emulsions, lysolecithin, polyols, polyanions and the like may be used to increase the immune response. One of ordinary skill in the art is able to construct a suitable antibody or recognition agent without undue experimentation.

In one embodiment, Western Blot analysis was used to detect the presence of phosphorylated p68 RNA helicase in a sample. Western blot analysis requires the use of sodium dodecyl sulfate-polyacrylamide gel electrophoresis (SDS-PAGE) and immunoblotting. To prepare the sample, the sample may be homogenized and protein extracts may be made from the homogenized sample.

The immunoreactivity or tumor-specific phosphorlyation of p68 RNA helicase also can be helpful in the diagnosis and treatment of cancer. For example, diagnostic procedures and screenings can be developed based on the presence of phosphylated p68 RNA helicase in sample cells. Further, the p68 RNA helicase phosphorylation in tumor cells provides a molecular target for the development of new anti-cancer drugs that are selectively activated by phosphorlated p68 RNA helicase in tumor cells.

After the p68 RNA helicase (whether phosphorylated or not) is separated from the sample by immunoprecipitation using antibodies against p68 RNA helicase, the level of p68 RNA helicase phosphorylation then may be determined by SDS-PAGE followed by Western Blot with antibody against phosphor-tyrosine. The intensity of the Western Blot signal corresponds to the level of p68 RNA helicase phosphorylation. This is an indirect method of detecting the presence of phosphorylated p68 RNA helicase.

Numerous procedures for using immunohistochemistry and ELISA to detect or test for phosphorylated p68 RNA helicase in a biological sample are known by persons with ordinary skill in the art or may be found readily in the literature by those with ordinary skill in the art. One preferred method is the use of Western Blots. Immunoassays such as antibody capture assays, two-antibody sandwich assays, and antigen capture assays also can be used in the present invention. Sample preparations for immunoassays include tissue fixation or homogenization, and protein extracts preparation. Immunoassays allow large numbers of samples to be tested relatively efficiently, and they offer quantitative precision.

Principles and practice of immunohistochemistry, Western Blot analysis, and other immunoassays are well known in the art.

Further, one strategy for the treatment of cancer may be to target the phosphorylated p68 RNA helicase in the cell or tissue. Based on the observations that (1) p68 RNA helicase was phosphorylated at tyrosine residues in cancer cells and cancer tissue and (2) p68 RNA helicase was not phosphorylated in normal cells and normal tissue, one cancer treatment involves the targeting of phosphorylated p68 RNA helicase. For example, it is possible that such a strategy to target the phosphorylated p68 RNA helicase could include introducing a competitor phosphorylated polypeptide that spans a region of a particular phosphorylated p68 RNA helicase.

More particularly, this competitor polypeptide may contain three functional parts. First, at the N-terminal, there can be 10-12 hydrophobic amino acids that can function as a cell-permeable sequence to direct the peptide into cells. Second, in the middle of the peptide, there can be a Nuclear Localization Signal (NLS). Third, at the C-terminal of the peptide, there can be about 16-22 amino acids from the p68 RNA helicase that spans the phosphorylation site or sites. The peptide then can be phosphorylated in vitro.

After the phosphorylated competitor peptide is purified, the competitor peptide can be used to treat the cancer cells or tissue. The introduction of such a competitor protein into cancer cells or tissues can result in changes in cell morphology, cell proliferation, cell adhesion, cancer cell invasion, and cancer cell migration. Such a treatment can be capable of regressing tumor growth and cancer metastasis.

While the functional role of tyrosyl phosphorylated p68 RNA helicase in cancer cells is an open question, drugs can be designed for, or screened for, specific metabolism by phosphorylated p68 RNA helicase in tumors. While the p68 RNA helicase protein is expressed in all tissue types, p68 RNA helicase was not phosphorylated at tyrosine residue(s) in cells derived from all normal tissues. Thus, it is clear that phosphorylated p68 RNA helicase is a marker for cancer and that the level of phosphorylated p68 RNA helicase is correlated with cancer metastasis.

The inventive concepts covered by this invention are illustrated in the following examples.

EXAMPLES

1. Exemplary Procedure

Preparation of Antibodies

Examples may use an antibody that recognizes human phosphorylated p68 RNA helicase epitopes. The polyclonal antibody PAbp68 and monoclonal antibody p68-rgg for p68 RNA helicase was raised against the C-terminal segment of recombinant p68 RNA helicase in rabbits and mice respectively. The antibody p-tyr-100 for tyrosine phosphate and 14B3 for threonine phosphate can be obtained from a commercial source.

Screening Method

The presence of phosphorylated p68 RNA helicase in cultured cells or tissue samples was examined using immunoprecipitation followed by Western Blots. Immunoblotting also was also performed with a monoclonal antibody against p68 RNA helicase to show the equal amounts or levels of p68 (phosphorylated and unphosphorylated) loaded in the western blotting. Such Western Blots include the use of antibodies to phosphorylated p68 RNA helicase and sodium dodecyl sulphate polyacrylamide gel electrophoresis (SDS-PAGE). Immunoblotting also was performed with a monoclonal antibody against p68 RNA helicase to show the presence of a positive control protein in tumor and normal samples and to indicate that there was no evidence of protein degradation in any of the tissue samples.

After the tissue samples were homogenized, the protein extracts were made from the homogenized sample. The tissue was screened for phosphorylated p68 RNA helicase in two steps. In the first step, the polyclonal antibody PAbp68 was used to isolate p68 RNA helicase from the extracts. In the second step, the antibody p-tyr-100 was used to detect the phosphorylated p68 RNA helicase from the total isolated p68 RNA helicase by the Western Blot. The intensity of the Western Blot signal by the antibody p-tyr-100, in the second step, corresponds to the level of phosphorylated p68 RNA helicase in the sample.

A polyacrylamide gel system was employed for separation of proteins. The cell nuclear extracts (80 µl) were diluted to 200 µl with RIPA buffer (160 mM NaCl, 20 mM Tris-HCl, pH 7.5, 1 mM EDTA, 1 mM EGTA, 1 mM DTT, 0.1% Triton X-100, 1% sodium deoxycholate, 0.1% SDS, 1 mM sodium vanadate, and 1 mM PMSF). The antibody PAbp68 then was added to the mixture. The solution subsequently was incubated at 4° C. for 4 hours. Protein A agarose bead slurry (40 µl) then was added and the mixture underwent rotation. The beads were recovered and washed with 5×600 µl RIPA buffer with 0.08% SDS. The precipitated proteins were analyzed by SDS-PAGE followed by Western Blot.

The Western Blot analysis was performed with a commercially available ECL Western Blot and detection kit (Amersham Biosciences). The supernatant from the culture medium of hybridoma cells P68-rgg were used in the blotting experiments at a 5:1 dilution. The polyclonal antibody PAbp68 was used in 1:3000 dilution. The antibodies, PY100 and 14B3 were used with 1:2000 dilution.

2. Exemplary Screening

Six cancer and seven non-cancer cells lines from various anatomical sites were screened using immunoassays to demonstrate that the presence of the phosphorylated p68 RNA helicase within a cell is able identify whether the cell is cancerous. These six cancer cells lines include lung carcinoma cells (A549), colonic tumor cells (Caco-2), hepatocellular carcinoma cells (HepG2), leukemia cells (K562), breast cancer cells (MCF-7), and cervix carcinoma cells (HeLa S3). The seven normal cells or tissues include normal human lung tissue, human embryonic lung cells (HEL299), human colon fibroblast cells (CCD-112CoN), normal human liver tissue, human normal breast cells (Hs578Bst), human B lymphocyte cells isolated from peripheral blood (RPM1788), and human embryonic kidney cells (HEK293). The cell lines or tissues are listed in Table 1.

The phosphorylation of p68 RNA helicase was investigated using HeLA S3, A549, HEL299, CCD-112CoN, HepG2, and MCF-7 cells. The HeLa S3 and A549 cells were grown in Ham's F12K medium supplemented with 10% fetal bovine serum. The HEL299, CCD-112CoN, HepG2, and MCF-7 cells were maintained in minimum essential medium supplemented with 10% fetal bovine serum. The culture medium contained 2 mM L-glutamine and Earle's BSS adjusted to contain 1.5 g/l of sodium bicarbonate, 0.1 mM of non-essential amino acids, and 1.0 mM sodium pyruvate. The Caco-2 cells were grown in a similar medium condition to that of HEL299 cells but supplemented with 20% fetal bovine serum. The RPMI 1788 and K562 cells were grown in Iscove's modified Dulbecco's medium supplemented with 10% fetal bovine serum. The HEK293 and Hs 578Bst cells were grown in modified Dulbecco's medium containing 10% fetal bovine serum. All cell culture medium contained penicillin (100 U/ml) and streptomycin (100 µg/ml). The cells were grown to 90% confluency prior to performing any experiment.

Table 1 shows the cell lines or tissue samples used in the screening. The cellular p68 RNA helicase was first immunoprecipitated from the fresh-made nuclear extracts using a polyclonal antibody PAbp68 raised against C-terminal of p68 RNA helicase.

TABLE 1

CANCER CELLS AND CORRESPONDING NORMAL CELLS/TISSUES USED IN SCREENING

|  | Lung | Colon | Liver | Lymphocyte | Breast | Kidney | Cervix |
|---|---|---|---|---|---|---|---|
| Cancer | A549 | Caco-2 | HepG2 | K562 | MCF-7 |  | Hela-S3 |
| Normal Tissue Samples | HEL299 Normal | CCD-12CoN | Normal | RPMI1788 | Hs578 Bst | HEK293 |  |

3. P68 RNA Helicase Tyrosyl Phosphorylation and Cancer

The correlation between the phosphorylation of p68 RNA helicase and cancer was investigated using a monoclonal antibody against phosphorylated-tryrosine (p-tyr-100).

Figure 1:
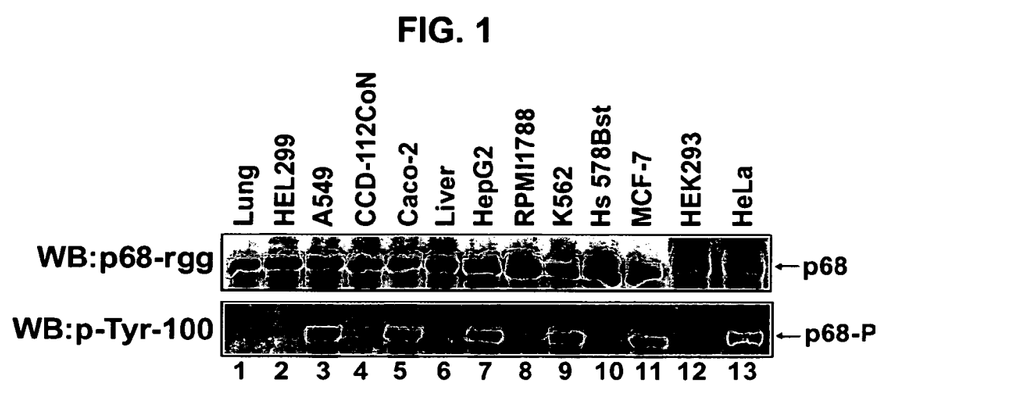
FIG. 1 shows Western Blots of the immunoprecipitated p68 RNA helicase from normal cells and from cancer cells.

FIG. 1 shows the immunoprecipitated p68 RNA helicase from normal and cancer cells probed using a monoclonal antibody against phosphor-tyrosine (p-tyr-100). P68 RNA helicase precipitated from nuclear extracts were prepared from all six cancer cell lines and were recognized by the antibody p-tyr-100 (top panel, lanes 3, 5, 7, 9, 11, and 13). P-tyr-100 did not recognize p68 RNA helicase immunoprecipitated from nuclear extracts prepared from the corresponding normal tissue or cells (bottom panel, lanes 1, 2, 4, 6, 8, 10, and 12). The tyrosine phosphorylation(s) in cancer cells was further confirmed by another monoclonal antibody against phosphorylated-tyrosine, PY20 (data not shown). Overall, this data indicates that phosphorylation of p68 RNA helicase at tyrosine residue(s) correlated with cancer development.

These preceding experiments demonstrate that there is a close correlation between p68 RNA helicase tyrosyl phosphorylation and cancer.

4. P68 RNA Helicase and Anticancer Agents

Figure 2A:
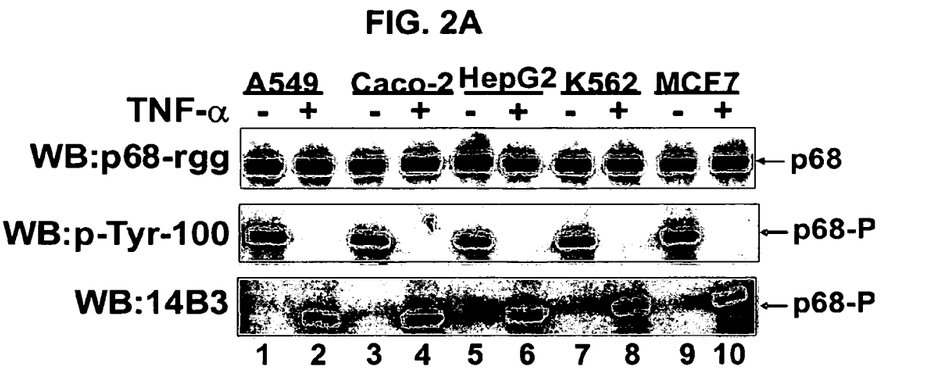
FIG. 2A shows Western Blots of immunoprecipitated cellular p68 RNA helicase from different cancer cells.

The effect of anticancer agents on the phosphorylation of p68 RNA helicase was investigated by exposing the cancer cells to anticancer agents STI-571 (Novartis), piceatannol (Sigma), etoposide (Calbiochem), and TAXOL® (USB). Among them, STI-571 and piceatannol are two different classes of protein tyrosine kinase (PTK) inhibitors. The etoposide is a DNA topoisomerase inhibitor, and TAXOL® is an antitumor drug that interacts with microtubules. Treatment of the six different cancer cell lines with STI-571, a BCR-Abl PTK inhibitor, led to dephosphorylation of p68 RNA helicase at tyrosine residue(s) (FIG. 2A, bottom panel, lines 2, 4, 6, 8). The exception was MCF-7, breast cancer cells, which there were observed decreases in the tyrosine phosphorylation level rather than complete dephosphorylation in MCF-7 cells (FIG. 2A, bottom panel, line 10).

The phosphorylations of p68 RNA helicase responded differently to different anticancer treatments. Tyrosyl phosphorylation(s) of p68 RNA helicase in HeLa cells could be dephosphorylated upon tumor necrosis factor alpha (TNF-α) treatment. TNF-α induces cell signal triggers cancer cell apoptosis. Tyrosine dephosphorylation of p68 RNA helicase can be an apoptotic marker of cancer cells in response to apoptosis inducing agents. The responses of tyrosine dephosphorylation of p68 RNA helicase in all six cancer cell lines to TNF-α (Peprotech) and TNF Related Apoptosis-Inducer Ligand (TRAIL) treatments suggests that the tyrosine dephosphorylation of p68 RNA helicase can be an apoptosis marker. The phosphorylation at tyrosine residue(s) upon the TNF-α and TRAIL treatments was monitored by the same immunoprecipitation and Western Blot procedure.

Figure 2B:
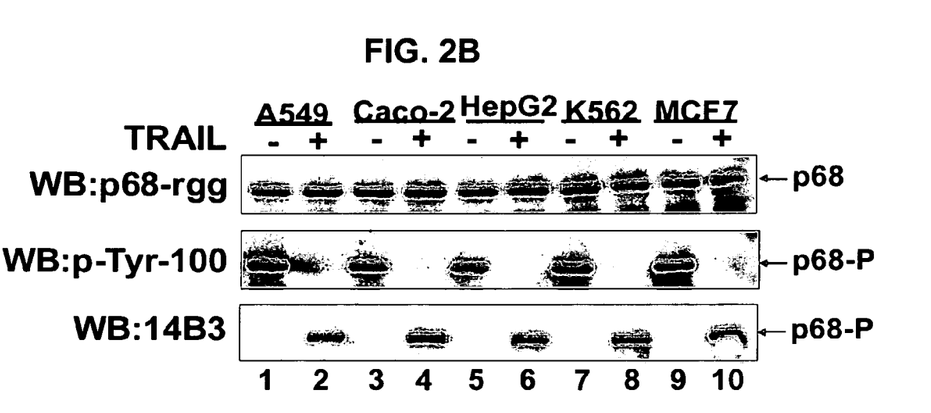
FIG. 2B shows Western Blots of immunoprecipitated cellular p68 RNA helicase from breast cancer cells.

FIGS. 2A and 2B show Western Blots of immunoprecipitated cellular p68 RNA helicase from different cancer cells (indicated). The immuno-blots were carried out using antibody p68-rgg (FIG. 2, top panel in A and B), antibody p-tyr-100 (middle panel in A and B), and antibody 14B3 (FIG. 2, bottom panel in A and B). The + and – represent with or without TNF-α or TRAIL treatments. Tyrosine dephosphorylation and threonine phosphorylation of p68 RNA helicase was present in cancer cells upon the panel (A) TNF-α or panel (B) TRAIL treatments.

As also shown in FIGS. 2A and 2B (middle panel, lane 2, 4, 6, 8, and 10), treatment of all six cancer cell lines with TNF-α or TRAIL led to the dephosphorylation of p68 at tyrosine residue(s). Interestingly, treatment of all six different cancer cells with TNF-α or TRAIL also resulted in phosphorylation of p68 at threonine (FIGS. 2A and 2B, bottom panel, lane 2, 4, 6, 8, and 10). Dephosphorylation at tyrosine residue(s) and phosphorylation at threonine residue(s) occurred at a very early stage of TNF-α or TRAIL treatments (within the first 10 minutes, data not shown). The threonine phosphorylation was quickly dephosphorylated again upon (30 minutes) treatment with TNF-α or TRAIL for a longer period of time (data not shown).

Figure 3A:
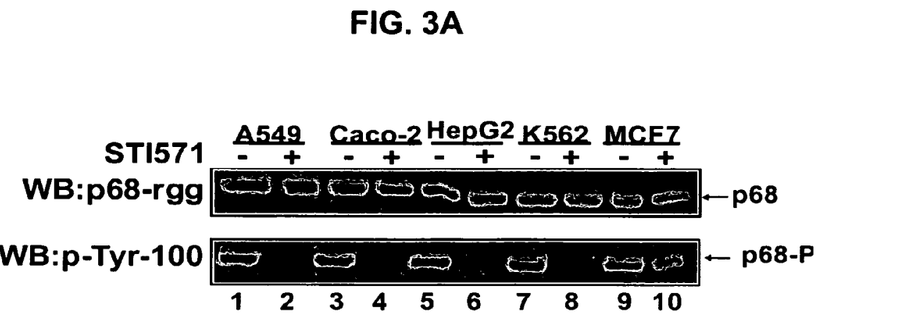
FIG. 3A shows Western Blots of immunoprecipitated cellular p68 RNA helicase from cells treated with an anticancer drug.

FIGS. 3A-3D show Western Blots of immunoprecipated cellular p68 RNA helicase from cells treated with the anticancer drugs STI-571, picetannol, epotoside, and TAXOL® on the tyrosyl phosphorylation of p68 RNA helicase. The Western Blots were carried out using antibody p68-rgg (top panel in FIG. 3A-3D) and antibody p-tyr-100 (bottom panel in FIGS. 3A-3D). The p68 RNA helicase was immunoprecipitated by antibody PAbp68. FIGS. 3A-3D show Western Blots of immunoprecipitated cellular p68 RNA helicase from different cancer cells (indicated on top) before (−) and after (+) treated with the anticancer drugs. There were observed decreases in the tyrosine phosphorylation level rather than complete dephosphorylation in MCF-7 cells (FIG. 3A, bottom panel, lane 10).

Figure 3B:
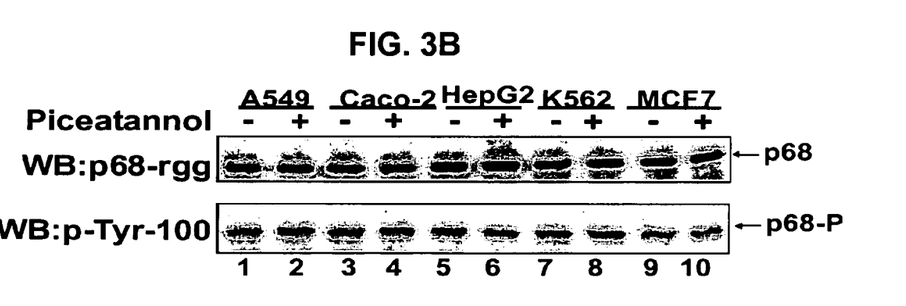
FIG. 3B shows Western Blots of immunoprecipitated cellular p68 RNA helicase from cells treated with piceatannol.
Figure 3C:
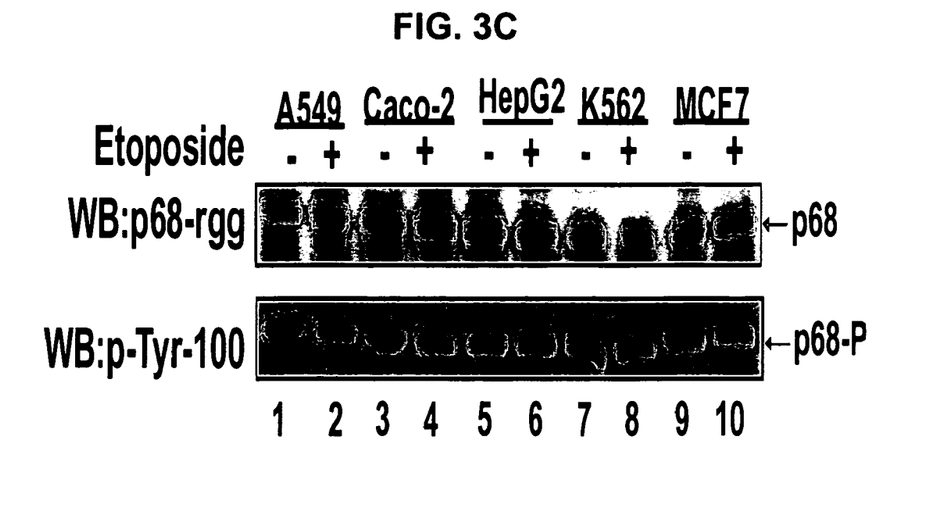
FIG. 3C shows Western Blots of immunoprecipitated cellular p68 RNA helicase from cells treated with etoposide.
Figure 3D:
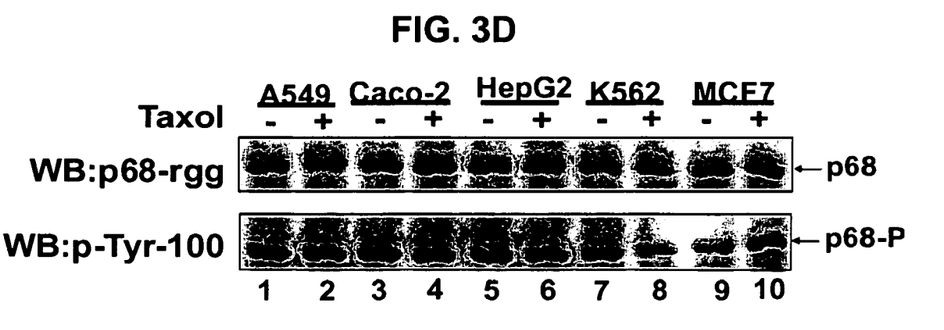
FIG. 3D shows Western Blots of immunoprecipitated cellular p68 RNA helicase from different cancer cells before and after treatment with various anticancer drugs.

FIGS. 3B-3D show that tyrosyl dephosphorylation was not observed when the cancer cells were treated with piceatannol, a syk PTK inhibitor, (FIG. 3B, bottom panel, lanes 2, 4, 6, 8, and 10), etoposide (FIG. 3C, bottom panel, lanes 2, 4, 6, 8, and 10), and TAXOL® (FIG. 3D, bottom panel, lanes 2, 4, 6, 8, and 10). Threonine phosphorylation was not detected upon the treatment with piceatannol, etoposide, and TAXOL® as observed with TNF-α and TRAIL (TNF-related apoptosis-inducing ligand) treatments (data not shown). This data demonstrates that the cancer cell specific tyrosine phosphorylation(s) of p68 RNA helicase responds differently to different anticancer treatments.

Thus, the phosphorylation of nuclear p68 RNA helicase can be useful in monitoring the treatment of cancer. The dephosphorylation response at tyrosine residue(s) occurs upon the treatment of TNF-α, TRAIL, or STI-571 drugs. The dephosphorylation at tyrosine residue(s) resulting from the anticancer drug treatment is useful in monitoring the effectiveness of anticancer drug treatments.

5. Levels of Phosphorylated P68 RNA Helicase and Metastatic Cancer

Cancerous and non-cancerous tissue or cells from various anatomical sites were screened using immunoassays to demonstrate that the level of phosphorylated p68 RNA helicase within the cell or tissue is able identify whether the cells or tissue are cancerous or metastatic. Lung cells, colonic cells, and ovarian cells were screened at different stages of cancer. In each of these cases, normal cells or tissue, adenocarcinoma (adenoCA) cells or tissue, and metastatic cells or tissue were screened for the presence and levels of phosphorylated p68 RNA helicase.

Figure 4A:
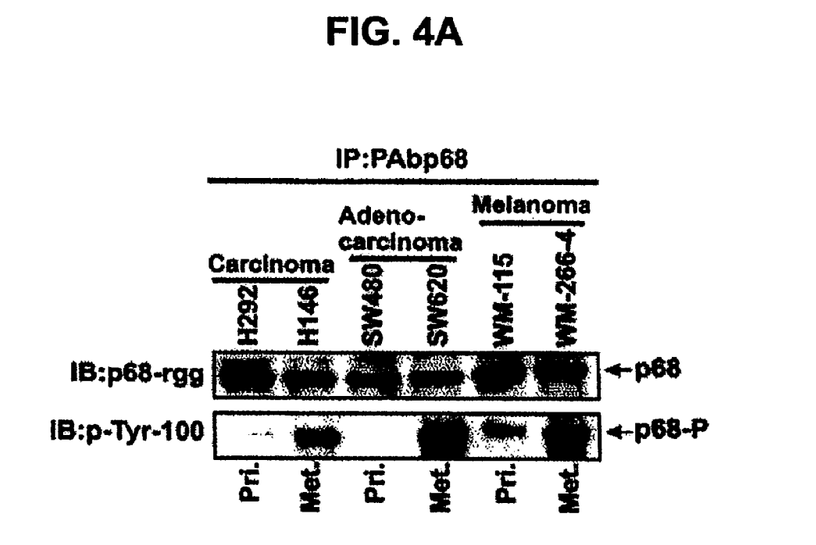
FIG. 4A shows Western Blots of immunoprecipitated phosphorylated p68 RNA helicase from cancer cells.

FIG. 4A shows Western Blots of immunoprecipitated phosphorylated p68 RNA helicase (at the tyrosine) from cancer cells derived from primary ("pri") cancer or metastatic cancer using p68-rgg or p-Tyr-100. Carcinoma cell lines, H292 and H146, are a pair of cancer cell lines derived from small cell lung cancer. H292 is derived from primary cancer and H146 is derived from small cell lung cancer (bone marrow metastasis). Adenocarcinoma cell lines, SW480 and SW620, are a pair of cancer cell lines derived from colon adenocarcinoma. SW480 is derived from primary cancer and SW620 is derived from colon cancer (lymph nodes metastasis). Melanoma cell lines, WM115 and WM-2664, are a pair of cancer cell lines derived from skin cancer. WM115 is derived from primary cancer, whereas WM266-4 is derived from metastatic cancer.

The level of phosphorylated p68 RNA helicase increases substantially as the cancer progresses from a primary carcinoma to metastasis. The primary cancer cells, which indicates non-metastatic cancer, shows a low level of phosphorylated p68 RNA helicase. Metastatic cancer cells shows a higher level of phosphorylated p68 RNA helicase than in the primary cancer cell lines. The level of phosphorylated p68 RNA helicase in metastatic cancer cells is substantially higher than that of non-metastatic cancer cells. As such, there is a clear correlation between the level of phosphorylated p68 RNA helicase in the tissue and the stage of cancer metastasis.

Figure 4B:
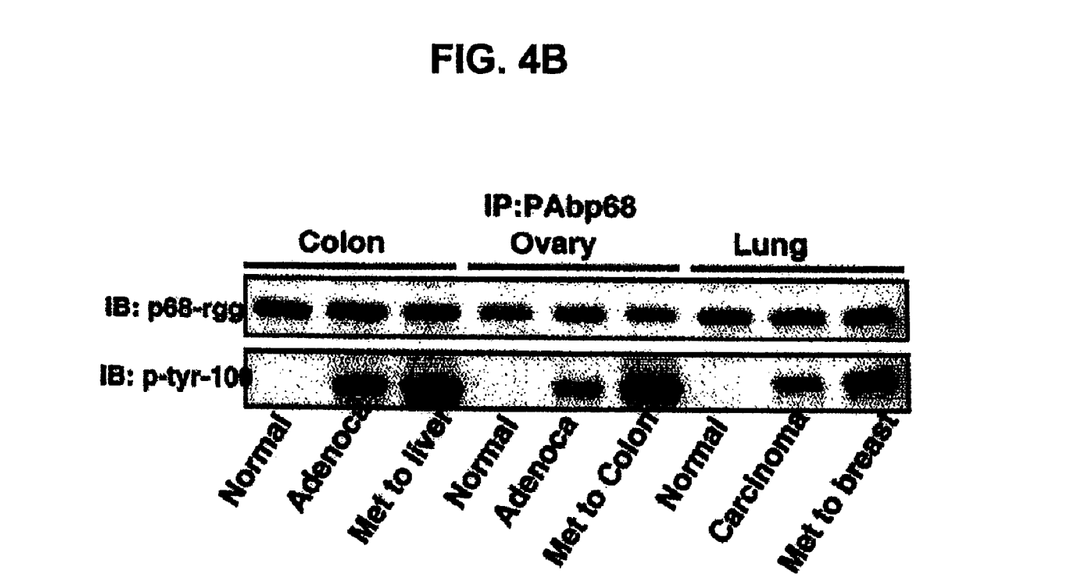
FIG. 4B shows Western Blots of immunoprecipitated cellular phosphorylated p68 RNA helicase from cell lines derived from metastatic or non-metatstatic cancer tissues, or tissue samples from cancer patients.

FIG. 4B shows Western Blots of immunoprecipitated phosphorylated p68 RNA helicase from normal, non-metastatic adenocarcinoma, and metastatic tissue samples from various anatomical sites including the colon, ovary and lung. Specifically, the normal tissue and the adenoCA tissue was derived from samples of non-metastatic adenocarcinoma tissues, and the metastatic tissue ("Met to" liver, colon, or breast) was derived from the secondary metastatic cancer tissue sites. The phosphorylated p68 RNA helicase at the tyrosine residue in each sample was screened using a combination of p68-rgg and p-Tyr-100 antibodies. The screened tissues originate from different cancer patients.

The results of the screening show that phosphorylated p68 RNA helicase can be a marker for cancer metastasis. As can be seen, the normal tissue in each line is negative for phosphorylated p68 RNA helicase. In contrast, the metastatic tissue has a very strong showing of phosphorylated p68 RNA helicase. As expected, the adenoCA tissue has less phosphorylated p68 RNA helicase than metastatic tissue, but clearly reflects the presences of phosphorylated p68 RNA helicase.

Figure 4C:
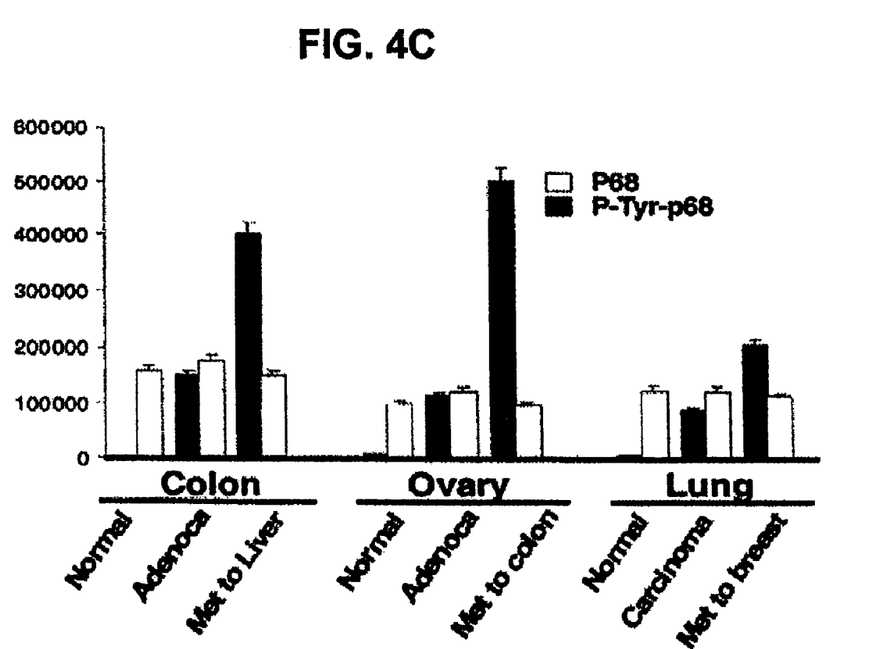
FIG. 4C shows a graph illustrating the relative level of phosphorylated p68 RNA helicase from normal, adenocarcinoma, and metastatic tissue.

FIG. 4C shows a graph of the quantity of phosphorylated p68 RNA helicase in each of the tissue samples shown in FIG. 4B. As can be seen, the level of phosphorylated p68 RNA helicase is substantially disparate from adenocarcinoma tissue and metastatic tissue. In each of the cases, the level of phosphorylated p68 RNA helicase was found to increase by at least two fold. Thus, the level of phosphorylated p68 RNA helicase in a tissue correlates well with the stages of cancer.

The foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

What is claimed is:

1. A method for determining the presence of lung, colon, liver, breast, kidney or cervical tumor cells in a cell sample comprising:
   obtaining a sample of cells from a host; and
   detecting whether phosphorylated p68 RNA helicase is present in the cell sample,
   wherein the cell sample is isolated from a tissue sample from a patient; and the presence of phosphorylated p68 RNA helicase in the cell sample, indicates the presence of lung, colon, liver, breast, kidney or cervical tumor cells.

2. The method as claimed in claim 1, further comprising;
   isolating p68 RNA helicase from the cell sample; and
   detecting whether phosphorylated p68 RNA helicase is present in the isolated p68 RNA helicase.

3. The method as claimed in claim 2, wherein the p68 RNA helicase is isolated using an antibody with specificity for the p68 RNA helicase.

4. The method as claimed in claim 3, wherein the phosphorylated p68 RNA helicase is detected using an antibody specifically binding to a phosphate group attached to a protein.

5. The method as claimed in claim 2, wherein the binding of the antibody to the phosphorylated p68 RNA helicase is detected using Western Blot techniques.

6. The method as claimed in claim 1, wherein the cell sample is derived from a lung, the colon, the liver, the blood a breast, a kidney, or the cervix of a host.

7. The method as claimed in claim 1, wherein the cell sample is a cell line.

8. The method as claimed in claim 7, wherein the cell line was isolated from a lung, the colon, the liver, the blood, a breast, a kidney or the cervix of a patient.

9. The method as claimed in claim 1, wherein an elevated level of phosphorylated p68 RNA helicase in the cell sample relative to a level of phosphorylated p68 RNA helicase in non-cancerous cells indicates the presence of abnormally proliferating cells in the cell sample.

* * * * *

SEQUENCE LISTING

```
<160> NUMBER OF SEQ ID NOS: 3

<210> SEQ ID NO 1
<211> LENGTH: 1845
<212> TYPE: DNA
<213> ORGANISM: Homo sapiens

<400> SEQUENCE: 1
atgtcgggtt attcgagtga ccgagaccgc ggccgggacc gagggtttgg tgcacctcga      60
tttggaggaa gtagggcagg gcccttatct ggaaagaagt ttggaaaccc tggggagaaa     120
ttagttaaaa agaagtggaa tcttgatgag ctgcctaaat ttgagaagaa tttttatcaa     180
gagcaccctg atttggctag gcgcacagca caagaggtgg aaacatacag aagaagcaag     240
```

-continued

```
gaaattacag ttagaggtca caactgcccg aagccagttc taaattttta tgaagccaat    300
ttccctgcaa atgtcatgga tgttattgca agacagaatt tcactgaacc cactgctatt    360
caagctcagg gatggccagt tgctctaagt ggattggata tggttggagt ggcacagacg    420
ggatctggga aaacattgtc ttatttgctt cctgccattg tccacatcaa tcatcagcca    480
ttcctagaga gaggcgatgg gcctatttgt ttggtgctgg caccaactcg ggaactggcc    540
caacaggtgc agcaagtagc tgctgaatat tgtagagcat gtcgcttgaa gtctacttgt    600
atctacggtg gtgctcctaa gggaccacaa atacgtgatt tggagagagg tgtggaaatc    660
tgtattgcaa caccttggaag actgattgac ttttttagagt gtgaaaaaac caatctgaga    720
agaacaacct accttgtcct tgatgaagca gatagaatgc ttgatatggg ctttgaaccc    780
caaataagga agattgtgga tcaaataaga cctgataggc aaactctaat gtggagtgcg    840
acttggccaa agaagtaag acagcttgct gaagatttcc tgaaagacta tattcatata    900
aacattggtg cacttgaact gagtgcaaac cacaacattc ttcagattgt ggatgtgtgt    960
catgacgtag aaaaggatga aaaacttatt cgtctaatgg aagagatcat gagtgagaag   1020
gagaataaaa ccattgtttt tgtggaaacc aaaagaagat gtgatgagct taccagaaaa   1080
atgaggagag atgggtggcc tgccatgggt atccatggtg acaagagtca acaagagcgt   1140
gactgggttc taaatgaatt caaacatgga aaagctccta ttctgattgc tacagatgtg   1200
gcctccagag ggctagatgt ggaagatgtg aaatttgtca tcaattatga ctaccctaac   1260
tcctcagagg attatattca tcgaattgga agaactgctc gcagtaccaa acaggcaca   1320
gcatacactt tctttacacc taataacata aagcaagtga gcgaccttat ctctgtgctt   1380
cgtgaagcta atcaagcaat taatcccaag ttgcttcagt tggtcgaaga cagaggttca   1440
ggtcgttcca ggggtagagg aggcatgaag gatgaccgtc gggacagata ctctgcgggc   1500
aaaagggggtg gatttaatac ctttagagac agggaaaatt atgacagagg ttactctagc   1560
ctgcttaaaa gagattttgg ggcaaaaact cagaatggtg tttacagtgc tgcaaattac   1620
accaatggga gctttggaag taattttgtg tctgctggta tacagaccag ttttaggact   1680
ggtaatccaa cagggactta ccagaatggt tatgatagca ctcagcaata cggaagtaat   1740
gttccaaata tgcacaatgg tatgaaccaa caggcatatg catatcctgc tactgcagct   1800
gcacctatga ttggttatcc aatgccaaca ggatattccc aataa                   1845
```

<210> SEQ ID NO 2
<211> LENGTH: 613
<212> TYPE: PRT
<213> ORGANISM: Homo sapiens

<400> SEQUENCE: 2

```
Met Ser Gly Tyr Ser Ser Asp Arg Asp Arg Gly Arg Asp Arg Gly Phe
1               5                   10                  15

Gly Ala Pro Arg Phe Gly Gly Ser Arg Ala Gly Pro Leu Ser Gly Lys
            20                  25                  30

Lys Phe Gly Asn Pro Gly Glu Lys Leu Val Lys Lys Trp Asn Leu
        35                  40                  45

Asp Glu Leu Pro Lys Phe Glu Lys Asn Phe Tyr Gln Glu His Pro Asp
    50                  55                  60

Leu Ala Arg Arg Thr Ala Gln Glu Val Glu Thr Tyr Arg Arg Ser Lys
65                  70                  75                  80

Glu Ile Thr Val Arg Gly His Asn Cys Pro Lys Pro Val Leu Asn Phe
                85                  90                  95
```

-continued

```
Tyr Glu Ala Asn Phe Pro Ala Asn Val Met Asp Val Ile Ala Arg Gln
            100                 105                 110

Asn Phe Thr Glu Pro Thr Ala Ile Gln Ala Gln Gly Trp Pro Val Ala
        115                 120                 125

Leu Ser Gly Leu Asp Met Val Gly Val Ala Gln Thr Gly Ser Gly Lys
    130                 135                 140

Thr Leu Ser Tyr Leu Leu Pro Ala Ile Val His Ile Asn His Gln Pro
145                 150                 155                 160

Phe Leu Glu Arg Gly Asp Gly Pro Ile Cys Leu Val Leu Ala Pro Thr
                165                 170                 175

Arg Glu Leu Ala Gln Gln Val Gln Gln Val Ala Ala Glu Tyr Cys Arg
            180                 185                 190

Ala Cys Arg Leu Lys Ser Thr Cys Ile Tyr Gly Gly Ala Pro Lys Gly
        195                 200                 205

Pro Gln Ile Arg Asp Leu Glu Arg Gly Val Glu Ile Cys Ile Ala Thr
    210                 215                 220

Pro Gly Arg Leu Ile Asp Phe Leu Glu Cys Gly Lys Thr Asn Leu Arg
225                 230                 235                 240

Arg Thr Thr Tyr Leu Val Leu Asp Glu Ala Asp Arg Met Leu Asp Met
                245                 250                 255

Gly Phe Glu Pro Gln Ile Arg Lys Ile Val Asp Gln Ile Arg Pro Asp
            260                 265                 270

Arg Gln Thr Leu Met Trp Ser Ala Thr Trp Pro Lys Glu Val Arg Gln
        275                 280                 285

Leu Ala Glu Asp Phe Leu Lys Asp Tyr Ile His Ile Asn Ile Gly Ala
    290                 295                 300

Leu Glu Leu Ser Ala Asn His Asn Ile Leu Gln Ile Val Asp Val Cys
305                 310                 315                 320

His Asp Val Glu Lys Asp Glu Lys Leu Ile Arg Leu Met Glu Glu Ile
                325                 330                 335

Met Ser Glu Lys Glu Asn Lys Thr Ile Val Phe Val Glu Thr Lys Arg
            340                 345                 350

Arg Cys Asp Glu Leu Thr Arg Lys Met Arg Arg Asp Gly Trp Pro Ala
        355                 360                 365

Met Gly Ile His Gly Asp Lys Ser Gln Gln Glu Arg Asp Trp Val Leu
    370                 375                 380

Asn Glu Phe Lys His Gly Lys Ala Pro Ile Leu Ile Ala Thr Asp Val
385                 390                 395                 400

Ala Ser Arg Gly Leu Asp Val Glu Asp Val Lys Phe Val Ile Asn Tyr
                405                 410                 415

Asp Tyr Pro Asn Ser Ser Glu Asp Tyr Ile His Arg Ile Gly Arg Thr
            420                 425                 430

Ala Arg Ser Thr Lys Thr Gly Thr Ala Tyr Thr Phe Phe Thr Pro Asn
        435                 440                 445

Asn Ile Lys Gln Val Ser Asp Leu Ile Ser Val Leu Arg Glu Ala Asn
    450                 455                 460

Gln Ala Ile Asn Pro Lys Leu Leu Gln Leu Val Glu Asp Arg Gly Ser
465                 470                 475                 480

Gly Arg Ser Arg Gly Arg Gly Met Lys Asp Asp Arg Asp Arg
                485                 490                 495

Tyr Ser Ala Gly Lys Arg Gly Asn Thr Phe Arg Asp Arg Glu Asn
            500                 505                 510
```

```
                              -continued

Tyr Asp Arg Gly Tyr Ser Ser Leu Leu Lys Arg Asp Phe Gly Ala Lys
        515                 520                 525

Thr Gln Asn Gly Val Tyr Ser Ala Ala Asn Tyr Thr Asn Gly Ser Phe
    530                 535                 540

Gly Ser Asn Phe Val Ser Ala Gly Ile Gln Thr Ser Phe Arg Thr Gly
545                 550                 555                 560

Asn Pro Thr Gly Thr Tyr Gln Asn Gly Tyr Asp Ser Thr Gln Gln Tyr
            565                 570                 575

Gly Ser Asn Val Pro Asn Met His Asn Gly Met Asn Gln Gln Ala Tyr
            580                 585                 590

Ala Tyr Pro Ala Thr Ala Ala Ala Pro Met Ile Gly Tyr Pro Met Pro
        595                 600                 605

Thr Gly Tyr Ser Gln
    610

<210> SEQ ID NO 3
<211> LENGTH: 4
<212> TYPE: PRT
<213> ORGANISM: Unknown
<220> FEATURE:
<223> OTHER INFORMATION: Description of unknown source of material:
      DEAD-box family of helicases, multiple organisms.

<400> SEQUENCE: 3

Asp Glu Ala Asp
1
```